(12) United States Patent
Van Tassel et al.

(10) Patent No.: US 7,235,096 B1
(45) Date of Patent: Jun. 26, 2007

(54) IMPLANTABLE DEVICE FOR PROMOTING REPAIR OF A BODY LUMEN

(75) Inventors: Robert A. Van Tassel, Excelsior, MN (US); David R. Holmes, Jr., Rochester, MN (US); Robert S. Schwartz, Rochester, MN (US)

(73) Assignee: TriCardia, LLC, Excelsior, MN (US)

( * ) Notice: Subject to any disclaimer, the term of this patent is extended or adjusted under 35 U.S.C. 154(b) by 554 days.

(21) Appl. No.: 09/382,275

(22) Filed: Aug. 25, 1999

Related U.S. Application Data

(63) Continuation-in-part of application No. 09/139,804, filed on Aug. 25, 1998, now abandoned.

(51) Int. Cl.
*A61F 2/06* (2006.01)

(52) U.S. Cl. .................. 623/1.15; 623/1.39; 623/1.41; 623/1.42

(58) Field of Classification Search ............... 623/1.1, 623/1.13, 1.15, 1.21, 1.39, 1.4, 1.41, 1.42, 623/1.43–1.48
See application file for complete search history.

(56) References Cited

U.S. PATENT DOCUMENTS

| | | | |
|---|---|---|---|
| 4,776,337 A | | 10/1988 | Palmaz |
| 5,059,211 A | | 10/1991 | Stack et al. |
| 5,078,736 A | * | 1/1992 | Behl ................... 623/1.15 |
| 5,439,446 A | | 8/1995 | Barry |
| 5,575,816 A | | 11/1996 | Rudnick et al. |
| 5,662,960 A | | 9/1997 | Hostettler et al. |
| 5,700,285 A | | 12/1997 | Myers et al. |
| 5,728,150 A | * | 3/1998 | McDonald et al. ........ 623/1.15 |
| 5,766,710 A | | 6/1998 | Turnlund et al. |
| 5,770,417 A | | 6/1998 | Vacanti et al. |
| 5,843,172 A | * | 12/1998 | Yan .......................... 623/1.42 |
| 5,879,604 A | | 3/1999 | Melbye et al. |

OTHER PUBLICATIONS

R.S. Schwartz et al., "Biomimicry, vascular restenosis and coronary stents," *SIIC*, 3(3-4):151-156, 1998.

D.A. Diechek et al., "Laboratory Investigation. Seeding of Intravascular Stents with Genetically Engineered Endothelial Cells," *Circulation*, 80:1347-1353, 1989.

* cited by examiner

*Primary Examiner*—Corrine McDermott
*Assistant Examiner*—Thomas J. Sweet
(74) *Attorney, Agent, or Firm*—Inskeep IP Group, Inc.

(57) ABSTRACT

An implantable stent having surface features adapted to promote an organized growth pattern of infiltrating cells when implanted in a tubular organ is provided. The surface features comprise depressions, pores, projections, pleats, channels or grooves in the stent body and are designed to increase turbulence or stagnation in the flow of a liquid, such as blood through the stent, and/or to promote the growth of infiltrating cells in an organized pattern. Alternatively, the invention stent can be populated with living cells prior to implant and can be heatable from an external source of energy, thereby inducing production of therapeutic bioactive agents from ingrowing cells. The invention also provides an implantable heatable stent for transcutaneously monitoring the flow of fluid through a lumen into which the stent is implanted by measuring the rate at which the heated stent cools in response to blood flow when the source of heat is removed.

79 Claims, 5 Drawing Sheets

IMPLANTABLE DEVICE FOR PROMOTING REPAIR OF A BODY LUMEN

RELATED APPLICATIONS

This application is a Continuation-In-Part application of U.S. patent application Ser. No. 09/139,804, filed Aug. 25, 1998, now abandoned which is incorporated herein by reference in its entirety.

BACKGROUND OF THE INVENTION

1. Field of the Invention

This invention relates generally to an implantable medical device; and more particularly to an implantable stent.

2. Discussion of the Prior Art

Damage to the endothelial and medial layers of a blood vessel, such as often occurs in the coarse of balloon angioplasty and stent procedures, has been found to stimulate neointimal proliferation, leading to restenosis of atherosclerotic vessels.

The normal endothelium, which lines blood vessels, is uniquely and completely compatible with blood. Endothelial cells initiate metabolic processes, like the secretion of prostacylin and endothelium-derived relaxing factor (EDRF), which actively discourage platelet deposition and thrombus formation in vessel walls. However, damaged arterial surfaces within the vascular system are highly susceptible to thrombus formation. Abnormal platelet deposition, resulting in thrombosis, is more likely to occur in vessels in which endothelial, medial and adventitial damage has occurred. While systemic drugs have been used to prevent coagulation and to inhibit platelet aggregation, a need exists for a means by which a damaged vessel can be treated directly to prevent thrombus formation and subsequent intimal smooth muscle cell proliferation.

Current treatment regimes for stenosis or occluded vessels include mechanical interventions. However, these techniques also serve to exacerbate the injury, precipitating new smooth muscle cell proliferation and neointimal growth. For example, stenotic arteries are often treated with balloon angioplasty, which involves the mechanical dilation of a vessel with an inflatable catheter. The effectiveness of this procedure is limited in some patients because the treatment itself damages the vessel, thereby inducing proliferation of smooth muscle cells and reocclusion or restenosis of the vessel. It has been estimated that approximately 30 to 40 percent of patients treated by balloon angioplasty and/or stents may experience restenosis within one year of the procedure.

To overcome these problems, numerous approaches have been taken to providing stents useful in the repair of damaged vasculature. In one aspect, the stent itself reduces restenosis in a mechanical way by providing a larger lumen. For example, some stents gradually enlarge over time. To prevent damage to the lumen wall during implantation of the stent, many stents are implanted in a contracted form mounted on a partially expanded balloon of a balloon catheter and then expanded in situ to contact the lumen wall. U.S. Pat. No. 5,059,211 discloses an expandable stent for supporting the interior wall of a coronary artery wherein the stent body is made of a porous bioabsorbable material. To aid in avoiding damage to vasculature during implant of such stents, U.S. Pat. No. 5,662,960 discloses a friction-reducing coating of commingled hydrogel suitable for application to polymeric plastic, rubber or metallic substrates that can be applied to the surface of a stent.

A number of agents that affect cell proliferation have been tested as pharmacological treatments for stenosis and restenosis in an attempt to slow or inhibit proliferation of smooth muscle cells. These compositions have included heparin, coumarin, aspirin, fish oils, calcium antagonists, steroids, prostacyclin, ultraviolet irradiation, and others. Such agents may be systemically applied or may be delivered on a more local basis using a drug delivery catheter or a drug eluting stent. In particular, biodegradable polymer matrices containing a pharmaceutical may be implanted at a treatment site. As the polymer degrades, a medicament is released directly at the treatment site. The rate at which the drug is delivered is dependent upon the rate at which the polymer matrix is resorbed by the body. U.S. Pat. No. 5,342,348 to Kaplan and U.S. Pat. No. 5,419,760 to Norciso are exemplary of this technology. U.S. Pat. No. 5,766,710 discloses a stent formed of composite biodegradable polymers of different melting temperatures.

Porous stents formed from porous polymers or sintered metal particles or fibers have also been used for release of therapeutic drugs within a damaged vessel, as disclosed in U.S. Pat. No. 5,843,172. However, tissue surrounding a porous stent tends to infiltrate the pores. In certain applications, pores that promote tissue ingrowth are considered to be counterproductive because the growth of neointima can occlude the artery, or other body lumen, into which the stent is being placed.

Delivery of drugs to the damaged arterial wall components has also been explored by using latticed intravascular stents that have been seeded with sheep endothelial cells engineered to secrete a therapeutic protein, such as t-PA (D. A. Dichek et al., Circulation, 80, 1347–1353, 1989). However, endothelium is known to be capable of promoting both coagulation and thrombolysis.

Another approach to controlling the healing of a damaged artery or vein is to induce apoptosis in neointimal cells to reduce the size of a stenotic lesion. U.S. Pat. No. 5,776,905 to Gibbons et al., which is incorporated herein by reference in its entirety, describes induction of apoptosis by administering anti-sense oligonucleotides that counteract the anti-apoptotic gene, bcl-x, which is expressed at high levels by neointimal cells. These anti-sense oligonucleotides are intended to block expression of the anti-apoptotic gene bcl-x so that the neointimal cells are induced to undergo programmed cell death.

Under certain conditions, the body naturally produces another drug that has an influence on cell apoptosis among its many effects. As is explained in U.S. Pat. No. 5,759,836 to Amin et al., which is incorporated herein by reference in its entirety, nitric oxide (NO) is produced by an inducible enzyme, nitric oxide synthase, which belongs to a family of proteins beneficial to arterial homeostasis.

However, the effect of nitric oxide in the regulation of apoptosis is complex. A pro-apoptotic effect seems to be linked to pathophysiological conditions wherein high amounts of NO are produced by the inducible nitric oxide synthase. By contrast, an anti-apoptotic effect results from the continuous, low level release of endothelial NO, which inhibits apoptosis and is believed to contribute to the anti-atherosclerotic function of NO. Dimmeler in "Nitric Oxide and Apoptosis: Another Paradigm For The Double-Edged Role of Nitric Oxide" (*Nitric Oxide* 1(4): 275–281, 1997) discusses the pro- and anti-apoptotic effects of nitric oxide.

In many instances it is desirable to prevent neointimal proliferation that leads to stenosis or restenosis. U.S. Pat. No. 5,766,584 to Edelman et al. describes a method for inhibiting vascular smooth muscle cell proliferation following injury to the endothelial cell lining by creating a matrix containing endothelial cells and surgically wrapping the matrix about the tunica adventitia. The matrix, and especially the endothelial cells attached to the matrix, secrete products that diffuse into surrounding tissue, but do not migrate to the endothelial cell lining of the injured blood vessel.

In the treatment of heart disease it is also important to determine the overall effectiveness of the heart as a pump and the ability of the blood vessels to carry blood to other organs. If blood flow to an organ is significantly restricted, the organ can be damaged, and if the flow is stopped, death may occur. Consequently, the measure of the flow of blood within a blood vessel has been used as an indicator of the condition of the blood vessel and the pumping action of the heart. By monitoring the blood flow of a patient, the early detection of a heart condition, or of restenosis, is possible, and preventative measures may be taken to address any problems. If the blood vessel becomes seriously clogged, angioplasty or a by-pass operation may be performed that uses a graft to circumvent the damaged vessel.

In overseeing the condition of a patient's blood vessel, a number of blood flow measurements may be needed, over time, to effectively monitor the patient's condition. One known method of monitoring the flow of blood in a vessel involves the percutaneous application of an instrument to measure the flow. Such methods are termed "invasive" because the body must be pierced to obtain the blood flow measurement. Clearly, invasive techniques to measure blood flow have a disadvantage in that the measurement must be taken under controlled conditions. For example, it is difficult, if not impossible, to monitor blood flow during periods of increased exercise.

Despite the progress of the art in providing implantable stents useful for treating a damaged body lumen, there is a need for new and better stents, particularly for stents that are adapted to promote growth of infiltrating cells into organized cellular structures, such as take place during angiogenesis and/or neovascularization, to aid in repair of a damaged body lumen. It is also apparent that a device that non-invasively measures the flow of blood in a blood vessel is desirable.

SUMMARY OF THE INVENTION

The present invention is based upon the discovery that neointimal proliferation can be promoted and turned to healing effect if the infiltrating cells can be forced to assume an organized growth pattern or by subjecting the cells to increased stress, such as temperature or fluid shear stress. Thus, contrary to present belief, in many instances in which it is desirable to encourage regrowth of a damaged blood vessel or other body lumen, such as a tubular organ, the natural phenomenon of neointimal proliferation occurring at a site of damage can be transformed from a cause of failure to a cause of healing.

Therefore, according to the present invention, there are provided stent(s) comprising a tubular stent body and having surface features sized and/or arranged to promote an organized growth pattern of infiltrating cells. For example, a film of cells covering at least the interior surface of the stent body may encourage ingrowth of infiltrating cells.

In many instances, the organized growth pattern develops into an organized cellular structure within the stent body to aid in repair of a damaged body lumen. For example, in one embodiment, the surface features are selected to promote angiogenesis when the stent is implanted intravascularly.

The surface features for promoting organized cell growth can comprise a plurality of depressions in the surface of at least a portion of the stent body, preferably arranged in a regular pattern on at least the interior surface of the stent body, such as a waffle weave. In other embodiments, the surface features comprise a plurality of pleats, ridges, channels or pores in the stent body wherein at least some of the pores run between the interior and exterior sides of the stent body (i.e., penetrate the stent body) and are sized to promote the organized cell growth.

In typical embodiments, the invention stent body is formed from a biocompatible polymer or a biocompatible metal with the surface features stamped or molded into the surface. For example, the invention stent body can be formed of a porous biocompatible material, such as a porous matrix of sintered metal fibers or a polymer wherein the pores are sized to promote the organization of ingrowing cells therein. Preferably, the invention stent is diametrically expandable for implant mounted upon such a device as a balloon catheter.

In other embodiments according to the present invention, there are provided stents having a surface feature that creates or enhances a condition of turbulence in a fluid flowing through the tubular stent body such that ingrowing cells are subjected to increased fluid shear stress by action of the turbulence, and/or the surface features create stagnant flow through the stent body sufficient to cause clotting of blood, thereby promoting angiogenesis and/or neovascularization within the stent body when the stent is implanted intravascularly.

For example, in one embodiment, at least a portion of the stent body is covered by a biocompatible substance that expands or thickens in an aqueous environment to assume a three-dimensional form that promotes turbulence within the stent body. The liquid-expandable substance can be applied to the stent body in a pattern, for example, a pattern of dots, lines or curvilinear markings. In one embodiment, the biocompatible substance is a biocompatible hydrogel, or a mixture thereof. Biocompatible hydrogels useful in manufacture of the invention stents are those that provide an interpenetrating polymer network (IPN) structure, which upon expansion in an aqueous environment, is characterized by the presence of interconnecting pores. If the stent body is itself formed of a fibrous mesh, there is communication between cells external to the stent (i.e., in the vessel or lumen wall) via the holes or pores in the stent body and those growing within the interconnecting pores of the hydrogel layer. Presently preferred hydrogels for use in fabrication of the invention stents are biodegradable hydrogels consisting of hydrophobic biodegradable polymers, (e.g., polylactide) and hydrophilic natural polymers (e.g., dextran) with an interpenetrating polymer network structure.

The stent body is designed to promote infiltration and population of the stent by living cells, when the stent is cultured in a cell-rich medium or when the stent is implanted into a blood vessel or other tubular body lumen in a living subject, such as a mammal. Further the surface features in the stent body are selected to cause the living cells that infiltrate and populate the stent to undergo cell growth in a specific pattern determined by the placing and dimensions of the surface features of the stent body. One example of such pre-determined cell growth pattern is angiogenesis and/or neovascularization.

The invention stent optionally further comprises a transcutaneously energized heating mechanism attached to the stent body. The heating mechanism, which can be energized remotely (i.e., transcutaneously), is adapted to controllably heat cells within and surrounding the stent in the lumen wall to a temperature sufficient to cause infiltrating cells, or cells seeded thereon prior to transplant, to increase production of one or more bioactive agents, such as one or more antiproliferative, anti-restenotic, apoptotic, or angiogenesis-stimulating agents. In one embodiment according to the present invention wherein the invention stent is implanted in a blood vessel, the heating mechanism includes from one to about six temperature sensors and is adapted to control the heating of the cells to an elevated temperature in the range of from 38° C. to about 49° C. However, in certain body lumens, such as the urinary tract, tracheobronchial tree, and the like, a temperature of 49° C. would cause damage. Therefore, those of skill in the art will be able to adjust the allowable maximum temperature to the body lumen being treated.

Upon application of external energy to the implanted stent, its temperature can be elevated to promote the production of beneficial molecules, such as nitric oxide, to effect a cessation of neointimal hyperplasia within the cells in the lumen wall and/or cells growing within the stent. Alternatively, the stent can be populated before implant with cells engineered to express a bioactive agent that promotes a healing bodily process, such as angiogenesis and/or neovascularization. Suitable bioactive agents that can be obtained from such genetically engineered cells include several growth factors, e.g., platelet derived growth factor-A (PDGF-A), transforming growth factor (TGF), nuclear factor-κβ (NF-κβ), an inducible redox-controlled transcription factor. In these studies, low levels of thermal therapy inhibited smooth muscle cell proliferation after balloon injury through suppression of growth factors PDGF-A and NF-κβ. If such cells are placed under the control of a heat sensitive promoter, such as a heat shock protein promoter, the heating mechanism can be used to switch on or off the production of the bioactive agent upon application or withdrawal of external energy to the implanted stent. Thus, the invention stent can be used in a number of different applications wherein it is desirable to chronically release a therapeutic substance from an implant, on demand, for example to cells within the wall of a damaged body lumen or tubular organ.

Accordingly, in another embodiment according to the present invention, there are provided methods for treating a tubular body organ in a subject in need thereof. The invention treatment method comprises promoting the ingrowth of living cells on a stent having surface features sized to promote ingrowth and/or orderly development of the cells, and implanting the stent into the tubular organ of the subject prior to or following the promoting of the ingrowth of the living cells so as to treat the tubular body organ. The living cells can be donor or autologous cells. The living cells can be provided by a donor or the cells can be autologous. The invention treatment method is particularly useful for promoting or inhibiting angiogenesis within the stent body.

In another embodiment, the invention stents are adapted for measuring the flow of a fluid through the stent body. In this embodiment, the invention stent comprises a tubular stent body and a transcutaneously energized heating mechanism attached to the stent body that includes at least two to about six temperature sensors attached at spaced locations along the length thereof, and a telemetering device for transcutaneously transmitting the output of the temperature sensors to an external monitor that records the output. Methods are provided for using the output from the temperature sensors to obtain the flow of a fluid, such as blood, through the stent body.

Thus, it is an object of the present invention to provide an implantable stent that is adapted to promote angiogenesis within a blood vessel or other tubular lumen into which the stent is implanted.

It is a further object of the present invention to provide an implantable stent that is adapted to enhance or stimulate neointimal infiltration, but with organization of the infiltrating cells so as to result in neovascularization.

It is a further object of the present invention to provide an implantable stent that is adapted to promote ingrowth of living cells, when cultured in a cell-rich in vitro environment or when implanted within a tubular body lumen, such as a blood vessel.

It is a further object of the present invention to provide a stent that creates stagnant flow and/or enhances shear turbulence in blood flowing therethrough when implanted into a blood vessel or other tubular body lumen (as compared with that applied by a similarly composed stent, but lacking the surface features of the invention stent).

It is a further object of the present invention to provide a living stent populated with living cells growing throughout pores and/or other surface features designed to promote growth of the cells into an organized cellular structure when the cell is implanted into a tubular body lumen or organ.

It is a further object of the present invention to provide such a living stent wherein the living cells are genetically engineered to produce a therapeutic bioactive agent, such as one selected to inhibit or promote angiogenesis or proliferation of intima within the implanted stent.

It is a further object of the present invention to provide a stent wherein there is attached or affixed thereto a mechanism for controlling heating of the stent in response to a transcutaneously applied energy source.

DESCRIPTION OF THE DRAWINGS

The foregoing features, objects and advantages of the invention will become apparent to those skilled in the art from the following detailed description, especially when considered in conjunction with the accompanying drawings in which like numerals in the several views refer to corresponding parts.

DETAILED DESCRIPTION OF THE INVENTION

Figure 1:
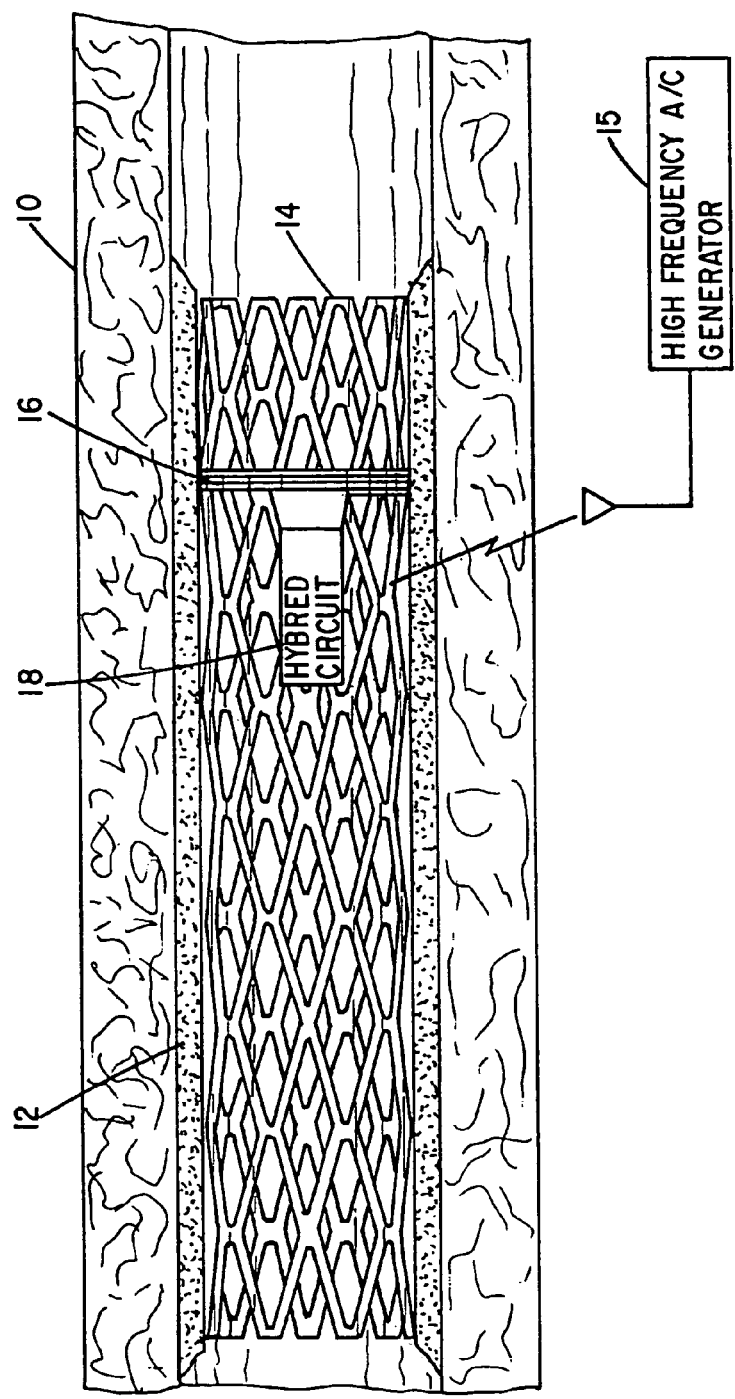
FIG. 1 is a greatly enlarged cross-sectional view through an artery showing a stent positioned therein, the stent including elements and/or circuitry for measuring and transmitting temperature information from the stent.

According to the present invention, there are provided stents comprising a tubular stent body having surface features adapted to promote an organized growth pattern of infiltrating cells, such as takes place during angiogenesis and/or neovascularization. For example, in one embodiment the surface features comprise a plurality of depressions in the surface of at least a portion of the stent body, for example the interior surface of the stent body. It is presently preferred that the surface depressions have an average volume per depression in the range from about 10 μm to about 100 μm. The surface depressions are generally arranged in an orderly pattern, such as a waffle weave pattern than can be readily stamped into the material from which the stent body is fabricated.

In one embodiment according to the present invention, the invention stent has surface features comprising pores in the stent body having an average diameter in the range from about 30 microns to about 65 microns. Generally the invention stent has a slightly greater inner diameter than that of the lumen into which it is placed such that a layer of ingrowing cells will cause the effective inner diameter to match the inner diameter of the vessel or lumen into which it is placed. Cells growing in the stent (e.g. in pores contained in the stent) will extend outward into the lumen of the stent and grow into attachment with cells in the lumen at either end of the stent, forming a continuous live cellular contact for fluid flow within the lumen of the stent. Since there would then be no contact with a foreign object in the vessel, thrombosis and immune response, which would tend to close the lumen of the stent with fibers and collagen, is reduced. Generally, the overall porosity of the invention stent is in the range from about 50% to about 85%, for example, at least about 70%.

It has been discovered that when the stent body is penetrated with pores having such an average diameter, the pores will be readily populated with living cells if the stent is cultured in a cell-rich medium (e.g., $6-10\times10^4$ endothelial cells in 0.8 ml culture medium) under cell-culturing conditions, as is known in the art. Such a cell culturing procedure is described, for example, in D. A. Dichek et al., supra, which is incorporated herein by reference in its entirety. Alternatively, if an invention stent having such pores is implanted into a body lumen, for example intravascularly, the implanted stent will readily be infiltrated by cells from the surrounding cellular environment so as to create an organized cellular structure similar to that of the surrounding bodily environment. For example, the type of organized structure formed within the stent may be dictated by the biological environment surrounding the implanted stent (e.g. whether a blood vessel or a urethra). Alternatively, the type of organized structure formed will correlate with the type of cells seeded into the stent or that infiltrate the stent from the implant site.

Surprisingly, it has been discovered that pores in the size range from about 30 microns to about 65 microns are particularly effective for promoting the growth and organization of infiltrating cells, such as cells of the vascular intima, into organized cellular structures, such as takes place during angiogenesis and neovascularization.

In another embodiment according to the present invention, the invention stent has surface features selected to organize the infiltrating cells into a longitudinal growth pattern. To promote this type of organized cell growth, the surface features of the invention stent can comprise a plurality of longitudinal pleats, grooves, channels, and the like, in the stent body (i.e., running along the axis of the tubular stent body). The pleats, grooves, or channels are preferably spaced and sized to create turbulence in flow of blood through the stent and/or to cause longitudinal alignment of cells that infiltrate the pleats, grooves, and/or channels. To encourage ingrowth of cells and cellular alignment, the pleats, grooves, or channels generally have an average height or depth in the range from about 10 μm to about 100 μm and an average distance from center to center in the range from about 10 μm to about 100 μm.

Alternatively, the surface features can be selected to create turbulence in a fluid, such as blood, flowing through the tubular stent body. For example, an undulating or uneven inner stent surface will enhance turbulence within the stent. The turbulence created by the surface features is intended to apply increased fluid shear stress on infiltrating cells (as compared with that applied by a similarly composed stent, but lacking the surface features of the invention stent) when the stent is implanted in the vasculature of a living body. Although the effect of fluid shear upon cell growth within a stent is not completely understood, it is believed that higher shear forces upon neointimal and endothelia slow or stop the cell growth. The elevated shear may force cells to mature earlier, the increased shear force being a mechanical and fluid dynamic stimulus to maturation. Preferably the fluid shear stress is created in the longitudinal direction relative to the stent.

In another embodiment according to the present invention, the invention stent has a tapered inner diameter for restricting fluid flow in a nozzle like manner, thereby tending to control cell growth by exerting increased fluid shear on the ingrowing cells.

It has also been discovered that angiogenesis and neovascularization are enhanced when blood flow through an implanted stent is slowed down sufficiently to promote clot formation, as clot formation is an initial step in the process leading to formation of new vasculature. Therefore, the surface features on the interior surface of the invention stent body can efficaciously be selected to promote stagnation of blood flow through the stent. There is evidence that smooth muscle cells migrate from sites distant to colonize a resorbing thrombus, using it as a bioabsorbable proliferation matrix in which to migrate and replicate. Typically, the thrombus is colonized at progressively deeper levels until the neointimal healing is complete R. S. Schwartz et al., "Biomimicry, vascular restenosis and coronary stents," *Semin Interv Cardiol* 3(3-4):151–6, 1998. Of course, formation of a thrombus can lead to downstream embolism. Therefore, care must be taken that the stagnation of flow is controlled in such a way as to avoid production of an embolism, for example, by adjustment of (i.e., by increasing) the fluid shear stress on the blood cells within the stent.

To aid in the creation of turbulence within the stent body that exerts fluid shear stress in a longitudinal direction on infiltrating cells, the surface features on the stent body can comprise an array of upstanding projections that promote or enhance shear turbulence in blood flow along at least a portion of the surface of the stent body (as compared with that applied by a similarly composed stent, but lacking the surface features of the invention stent). Preferably the array covers at least the interior surface of the stent body. The projections generally have an average height of from about 10 μm to about 100 μm. In one embodiment, the projections comprise an orderly array of hooks, such as is used in Velcro® fasteners, or stalks having a diameter to height ratio of from about 10:1 to about 100:1. Generally such stalks have a flow impeding feature, such as a bulbous tip. The orderly array can have a uniform spacing of from about 10 µm to about 200 µm from center to center. Methods for fabricating a flexible backing having an array or such projections are disclosed in U.S. Pat. No. 5,879,604, which is incorporated herein by reference in its entirety.

In another embodiment according to the present invention, the surface features on the invention stent comprise a layer of a biocompatible substance that expands or thickens in an aqueous environment to assume a three-dimensional form, wherein the layer covers at least a portion of the surface of the stent body. For example, the biocompatible substance can be or comprise one or more hydrogels, such that the hydrogel layer expands as it absorbs water upon contact with an aqueous environment to create a porous three dimensional layer. Alternatively, the three dimensional form can comprise an array of upstanding projections, such as described above. In this case, it is preferred that the surfaces of the stent be relatively smooth (e.g., with the projections lying recumbent against the surface of the stent body or in an undeveloped state) until such time as the stent is implanted and/or comes into contact with an aqueous environment. For example, the projections can be formed from dots of a substance that expands upon contact with water, such as dots of hydrogel or calcium hydroxyapatite crystals upon at least the interior surface of the stent body that expand upon contact with an aqueous environment, thereby forming projections into the interior void of the stent body. Such projections aid in slowing the flow of fluid through the stent body. In another embodiment according to the present invention, the surface features on the invention stent comprise a pattern of hydrogel markings on at least a portion of the surface of the stent body, such as a pattern of dots, lines, curvilinear tracings, or a mixture thereof. Preferably the markings are distributed over at least the interior surface of the stent body, but the pattern of markings can also cover the exterior surface of the stent body.

The stent body can be formed of any suitable substance, such as is known in the art, that can be adapted (e.g., molded, stamped, woven, etc.) to contain the surface features described herein. For example, the stent body can be formed from a biocompatible metal, such as stainless steel, tantalum, nitinol, elgiloy, and the like, and suitable combinations thereof.

Preferred metal stents are formed of a material comprising metallic fibers uniformly laid to form a three-dimensional non-woven matrix and sintered to form a labyrinth structure exhibiting high porosity, typically in a range from about 50 percent to about 85 percent, preferably at least about 70 percent. The metal fibers typically have a diameter in the range from about 1 micron to 25 microns. The average effective pore size is in the stent body such that cellular ingrowth into the pores and interstices is enhanced, for example having an average diameter in the range from about 30 microns to about 65 microns. A material having these desired properties that can be used in manufacture of the invention stent is available from the Bekaeart Corporation of Marietta, Ga., and sold under the trademark, BEKIPOR® filter medium.

Alternatively, the stent body can be formed of a biocompatible non porous polymer or a polymer made porous by incorporating dissolvable salt particles prior to curing thereof and then dissolving away the salt particles to leave voids and interstices therein. The polymer may be biostable or bioabsorbable, such as a number of medical grade plastics, including but not limited to, high-density polyethylene, polypropylene, polyurethane, polysulfone, nylon and poly-tetra-fluoroethylene. A porous polymer stent body can be made having pores with an average diameter in the range from about 30 microns to about 65 microns, by procedures known in the art. For example, polymer granules can be ground down to obtain small particles of about 100 microns in diameter, mixed with salt, and compressed into a compact form, for example using a jack, a plate and a die. The compressed forms are then placed in a pressure vessel and subjected to a gas, such as carbon dioxide, at high pressure of about 800 pounds per square inch until the gas dissolves into the polymer, the pressure is released rapidly, and the polymer particles expand and fuse together, to yield a porous polymer. Finally, the salt is leached out of the polymer to obtain a polymer having up to about 85 percent porosity.

Autologous cells naturally invade the invention stent, particularly the surface features thereof, following placement in a body lumen of a host subject and spontaneously generate an organized cellular structure that varies depending upon the cellular makeup of the bodily lumen into which the stent is implanted. Alternatively, endothelial or other suitable cells may be made to invade the stent in a cell culture lab to create a living stent prior to implant, using methods known in the art. For example, a living stent can be obtained according to the invention wherein the stent is populated with live cells selected from endothelial cells, smooth muscle cells, leukocytes, monocytes, epithelial cells, polymorphonuclear leukocytes, lymphocytes, basophils, fibroblasts, stem cells, epithelial cells, eosinophils, and the like, and combinations of any two or more thereof. In the invention living stent, such cells actually live within the surface features of the stent, such as the pores, grooves, channels, etc., and are not merely a surface coating, as may be the case when a metal wire braided stent is used, or other stent lacking suitable surface features as disclosed herein.

To enhance in vitro invasion of selected live cells, the stent may first be coated with a suitable component, such as a protein like fibronectin, elastin, mucopolysaccharide, or other suitable extracellular matrix protein. The thus-treated stent is placed in a cell culture dish and the selected living cells are allowed to form a coating on non-porous stents and to invade the interior of a porous stent material. Once the stent is populated with living cells, it is ready for implant.

Without limitation, in overall size a typical intravascular stent may have an outer diameter in a range of from about 2.0 mm to about 6.0 mm and a wall thickness in a range from about 0.1 mm to about 12 mm, for example about 0.1 mm to about 1.0 mm. The particular size, of course, depends on the anatomy where the stent is to be implanted.

In another embodiment, the invention stent is diametrically adjustable, being designed to be remotely introduced into a body cavity by the use of a catheter type of delivery system. Any of a variety of techniques or designs, as is known in the art, can be used for making the invention stent diametrically expandable. For example, such designs are disclosed for example in U.S. Pat. No. 5,059,211, which discloses an expandable stent made of a porous polymeric material. Alternatively, the stent body can be made of an expanded metal or plastic device having a fenestrated side wall to facilitate expansion thereof, as shown in FIG. 1. In yet another embodiment, the stent may instead have a tubular configuration that is pleated longitudinally prior to implant so as to exhibit a reduced outside diameter to facilitate routing and placement thereof, but which may later be expanded to a diameter equal to or only slighter greater than the diameter of the blood vessel, body lumen, or tubular organ at the treatment site. The stent may also have a rolled or braided construction known in the art which can be expanded from a lesser diameter to a larger diameter.

The diametrically expandable stent is designed to be implanted in a contracted form, for example, mounted on a partially expanded balloon of a balloon catheter and then expanded in situ to contact the lumen wall. Although any appropriate ratio between the collapsed and expanded diameters of the invention stent can be employed, depending upon the body lumen into which the stent is to be placed, generally in the diametrically adjustable stent, the expanded diameter is at least about 1.5 times the size of the collapsed diameter. Optionally, the invention stent can be coated with a friction-reducing coating, for example of commingled hydrogel, to reduce friction during implant, as disclosed in U.S. Pat. No. 5,662,960.

Referring to FIG. 1, there is illustrated a greatly enlarged cross-sectional view, through an arterial blood vessel 10. Formed within the blood vessel is a stenotic lesion 12 that has been subjected to balloon angioplasty for establishing greater patency to the artery. In carrying out the balloon angioplasty procedure, the blood vessel has been damaged, and a stent 14 constructed of a material capable of supporting cellular growth thereon, has been implanted into the lumen of the blood vessel and expanded to abut the inner layer of the injured blood vessel.

Figure 2:
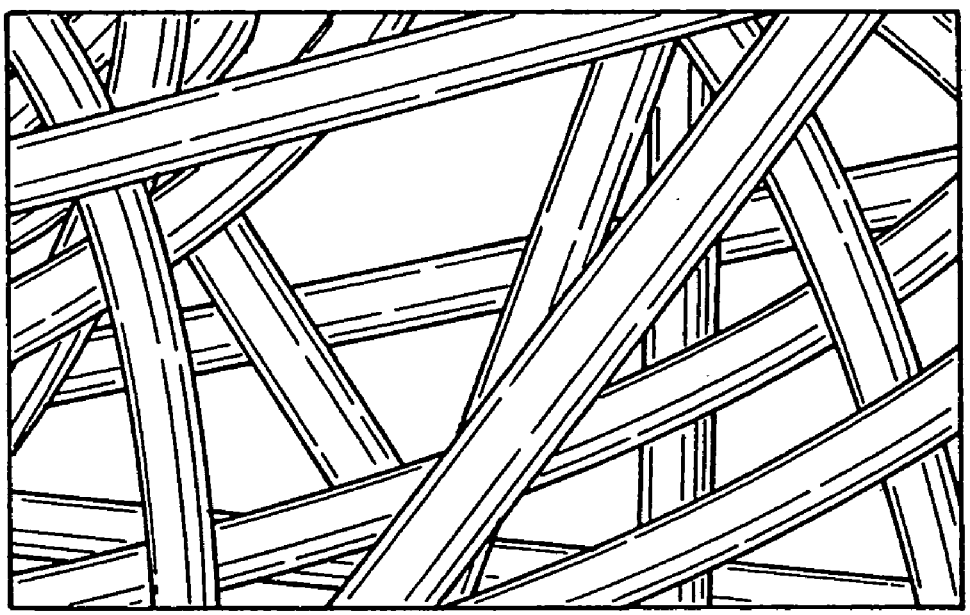
FIG. 2 is a greatly enlarged cross-sectional view of a preferred material from which a stent like that shown in FIG. 1 may be formed.

Stent 14 is preferably a balloon expandable device made of expandable metal or braided wire, but also may be designed as a self-expanding structure. It may also be fabricated from a composition of metallic fibers, uniformly laid to form a three-dimensional, non-woven structure, such as is shown in FIG. 2.

In accordance with the present invention, the invention stent may be used as part of a stent system which comprises, in addition to the invention stent, an energy source for transcutaneously transmitting heating energy to the stent to raise the temperature of the implanted stent to a temperature above body temperature. The energy source is external to the subject and delivers electromagnetic energy to the stent in the form of radio frequency energy, microwave energy, a magnetic field, and the like. The percutaneously delivered electromagnetic energy is transformed to heat energy in the stent body itself, for example through induction of Eddy currents or dielectric heating. Optionally, but preferably, delivery of energy to the stent, and consequently heating of the stent, is controlled by from one to about six heat sensors attached to the stent body that communicate percutaneously with the energy source to regulate the heating of the stent to a safe level. Preferably the energy source can transmit sufficient energy to the implanted stent to stimulate the live cells therein to increase production of one or more bioactive agents, such as are effective to modify vascular structure in the hematologic system. For example, if the ingrowing cells produce heparin, a coating of heparin will be formed on the stent surface that modifies platelet function.

For example, where a metal stent is employed, the energy source for transcutaneously transmitting heating energy to the invention stent can comprise a source of high frequency AC current, shown here as generator 15, for externally applying an alternating electromagnetic field that is transcutaneously transmitted from generator 15 to the implanted stent 14 so as to induce Eddy currents therein, thereby causing the temperature of the stent to rise above normal body temperature. To avoid the need for telemetry, if the stent is made of a suitable metal alloy exhibiting a Curie point at a desired maximum temperature of about 49° C. or less, no control need be maintained over the externally applied magnetic field because the heating of the stent will not increase above the point corresponding to the Curie point. Similarly, in the case of a polymer stent, the source of transcutaneously applied heating energy can comprise a source of microwave energy, or another form of high frequency dielectric heating known in the art, for transcutaneously generating heat in the polymer stent.

In another embodiment according to the present invention, the invention stent used in the stent system as disclosed herein further comprises a thermostat/heat regulator for monitoring the temperature of the implanted stent and regulating the temperature therein to avoid over-heating of the stent and cells living therein to a temperature where cell necrosis occurs, as described above. For example, FIG. 1 shows the thermostat/heat regulator as an electronic sensor and telemetering device comprising antenna coil 16, which is wrapped about the surface of the stent 14, the antenna coil being connected to a hybrid integrated circuit chip 18, which is also mounted on the surface of the stent. When the source of high frequency energy used in the invention stent system to transcutaneously transmit energy to the invention stent is a radio frequency generator, a portion of the RF energy used in heating the stent 14 is picked up by the antenna coil 16 and converted to a DC voltage for powering the electronics comprising the hybrid circuit. Alternatively, a metal stent body may itself act as an antenna and transfer energy to a temperature sensor sufficient to activate the sensor and transmit temperature readings to a transcutaneous monitor, and the like.

Figure 3:
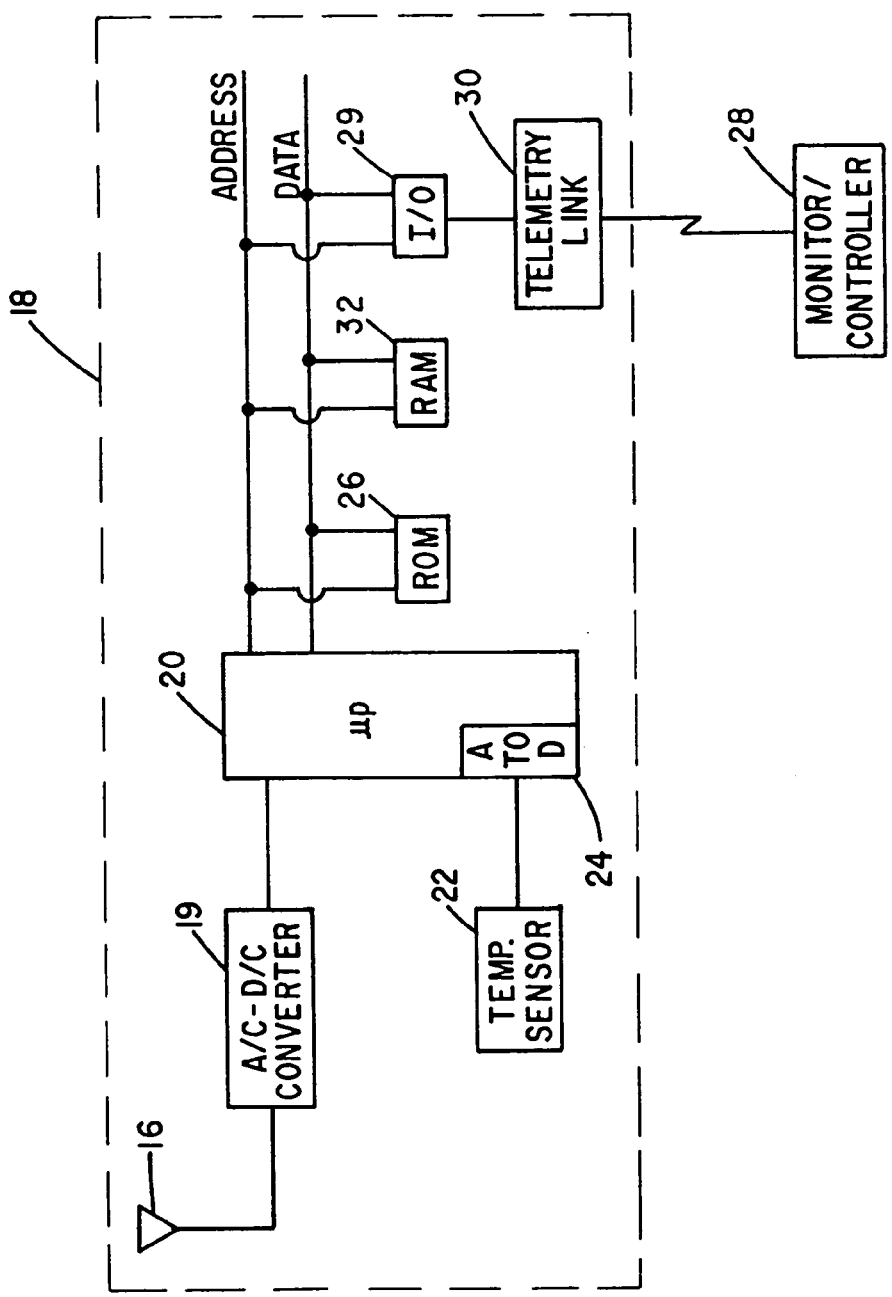
FIG. 3 is a schematic block diagram of the system used with the stent of FIG. 1.

FIG. 3 is a schematic diagram of a representative hybrid circuit and it shows an AC/DC converter 19 for producing a DC voltage for powering the microprocessor 20. A temperature sensor, such as a thermistor bead 22, is applied to the microprocessor and more particularly to an on-chip A/D converter 24 to produce a binary signal train proportional to the difference between stent temperature and body temperature.

A program for controlling the conversion of the analog output from the temperature sensor 22 to a digital representation is stored in a ROM memory 26 in the hybrid circuit 18 and the data may be transmitted to an external monitor/controller 28 by means of a telemetry link 30 of conventional design known in the art. The monitor/controller will then operate to increase or decrease the energy being transcutaneously delivered to the stent by the high frequency AC generator such that the stent temperature can be maintained at a predetermined set-point value previously programmed into the RAM memory 32 of the hybrid circuit 18.

The temperature sensor can be a passive heat sensor, such as a temperature sensitive crystal, affixed to the stent and when an interrogation frequency is applied, via an external power source, such as a generator, the crystal will resonate at a frequency that varies with temperature.

Our experiments have shown that elevated temperatures in the range of from about 38° C. to about 49° C. will induce production of positive enzymes and bioactive agents as gene products in certain cells located in and near the stent. For example, heat shock proteins and NOS can be generated in smooth muscle cells. At these temperatures, the forming neointimal cells in the surface features of the invention stent exhibit an upregulation of useful proliferation-inhibitory products as neointima forms in the surface features (i.e. pores) of the stent and in the vessel wall contacted by the stent. However, temperatures in excess of about 49° C. may result in cell necrosis and terminate production of beneficial gene products. In addition, nitric oxide synthase, the enzyme known to trigger production of nitric oxide in endothelial cells of the vasculature, among others, has been found to be a by-product of hyperthermia and NO has been shown to be shown to produce apoptosis inhibiting proliferation of smooth muscle cells.

Experiments we have conducted have demonstrated that cyclic, low level heat treatment reduced proliferation of cells following vascular injury in an organ culture model of porcine coronary arteries. While the exact mechanism whereby intimal hyperplasia is reduced is not clear, it is known to be related to smooth muscle cell proliferation, which, in turn, is controlled by several growth factors, e.g., platelet derived growth factor-A (PDGF-A), transforming growth factor (TGF), nuclear factor-$\kappa\beta$ (NF-$\kappa\beta$), an inducible redox-controlled transcription factor. In these studies, low levels of thermal therapy inhibited smooth muscle cell proliferation after balloon injury through suppression of growth factors PDGF-A and NF-$\kappa\beta$.

Figure 4:
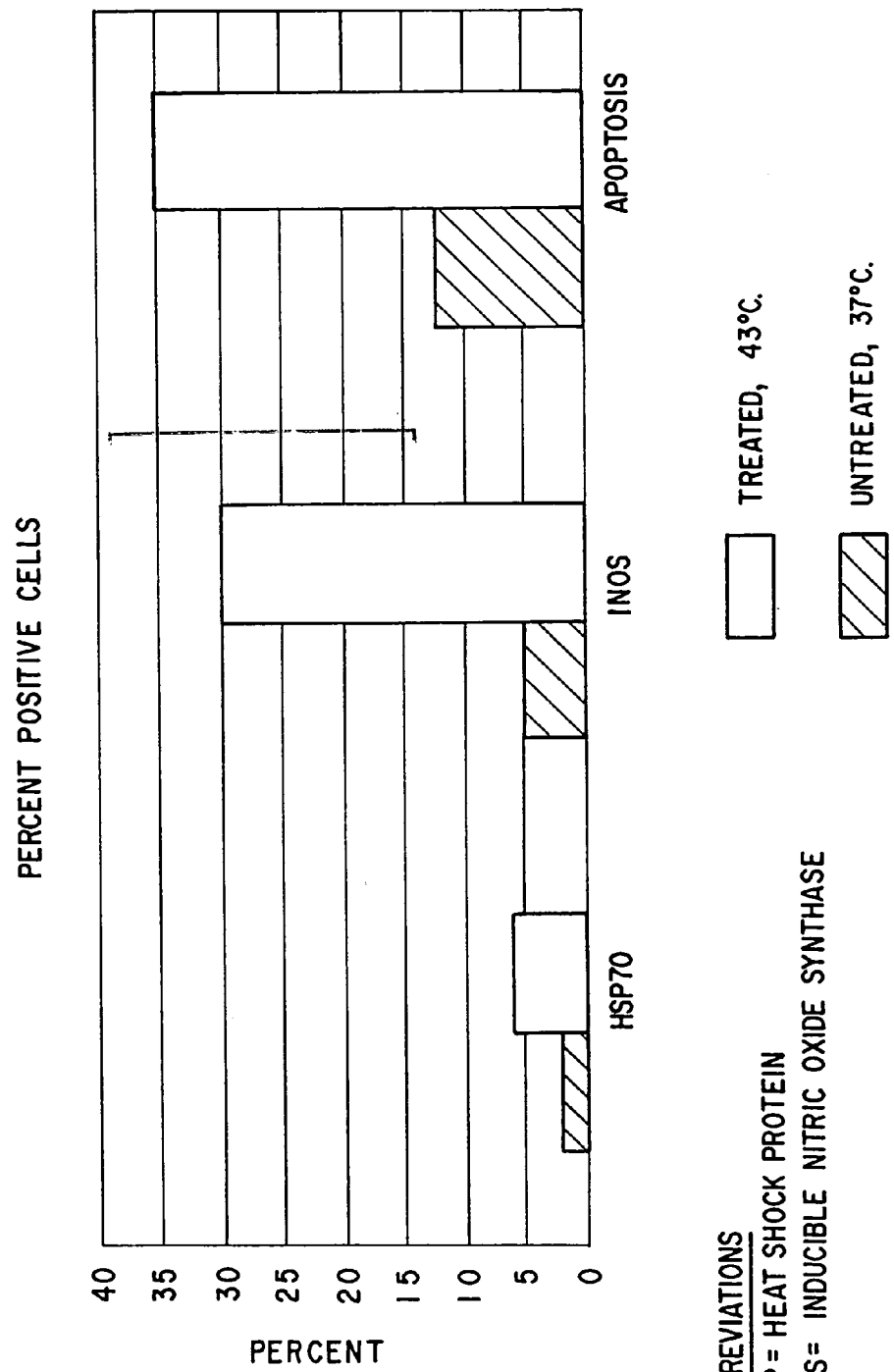
FIG. 4 is a bar chart graph showing the percentage increase in cell production of heat shock protein and inducible nitric oxide synthase resulting from the hyperthermia.

The graph of FIG. 4 illustrates the up-regulation in a heat shock protein, HSP70, and inducible nitric oxide synthase resulting from an increase in the cell temperature from 37° C. to 43° C. Also shown is the corresponding increase in apoptosis in smooth muscle cells.

Accordingly, in another embodiment of the present invention, there are provided methods for treatment of a tubular body organ in a subject in need thereof. The invention treatment method comprises promoting the ingrowth of living cells in a stent having surface features sized and/or arranged to promote ingrowth of the cells, and implanting the stent into the tubular organ of the subject prior to or following the promoting of the ingrowth of the living cells so as to treat the tubular body organ. The invention stent used in the treatment method holds the cells in a specific pattern or stimulates the growth of the cells into an organized growth pattern. Preferably, the organized growth pattern develops into an organized cellular structure within the stent body, such as takes place during angiogenesis and/or neovascularization. The living cells can be either donor or autologous cells.

The stent of the present invention can be implanted using any surgical technique known in the art as is dictated by the particular tubular body organ to be treated. However, it is presently preferred to implant the invention living stent by placing the device in an unexpanded form over a deflated balloon on the distal end of an intravascular catheter. The catheter is routed through the vascular system until the stent is positioned adjacent to target tissue where the balloon is then inflated to expand the stent against the wall of the blood vessel. Once the stent is lodged in place, the balloon is again deflated and the placement catheter is withdrawn from the body.

The invention treatment method can be used to stimulate the growth and/or repair of numerous tubular body organs, including, but not limited to blood vessels, trachea, ureters, urethrea, the common bile duct, the bronchi, and the like. So long as the body lumen has not suffered a circumferential lesion that completely destroys or disrupts the integrity of the lumen, the invention stent can be used to repair most types of injuries in a tubular body lumen, including tears, splits, and the like.

In another embodiment of the invention treatment method, wherein the stent further comprises a transcutaneously energized heating mechanism, the invention treatment method further comprises transcutaneously applying energy to the stent, thereby heating the stent to a temperature above normal body temperature sufficient to cause the living cells to express one or more bioactive agents.

The invention treatment method can be self-administered. For example, after the stent has been placed into the body lumen, either percutaneously or surgically, the subject can place the energy source on or next to the outer body surface proximal to the stent so as to place the stent in the energy field. For example, if the stent has been placed into a coronary artery, the subject would hold the energy source against the surface of the chest. If the stent comprises a thermostat/heat regulator as described herein, or as known in the art, the sensor in the implanted stent will regulate the energy field produced by the energy source as needed to modulate the temperature of the stent and surrounding tissue to the desired temperature range (i.e. above body temperature, but below the temperature at which necrosis will occur).

The treatment can comprise operating the energy source with the stent in the energy field for a single period of time, or at repeated short intervals, for example about 20 to 30 minutes per day. The treatment can be continued in this manner for as long as desired, for example, over a period of weeks or even months.

The living cells ingrowing in the stent in the invention treatment method, which produce beneficial bioactive agents can be autologous cells of the subject into which the stent is implanted, cells seeded into the stent prior to implant that naturally produce the desired bioactive agent, or cells that are genetically modified to produce a desired bioactive agent. Living cells that naturally produce one or more bioactive agents useful in practice of the invention methods include endothelial cells, smooth muscle cells, leukocytes, monocytes, polymorphonuclear leukocytes, lymphocytes, basophils, fibroblasts, stem cells, epithelial cells, eosinophils, and the like, and suitable combinations thereof. Such cells can be either donor or autologous cells.

Alternatively, the cells used in the invention treatment method can be engineered to express and release a bioactive agent in response to heating above body temperature such that the recombinant gene products are delivered to a site implanted with an invention stent. For example, a heat sensitive gene promoter can be operatively associated with a gene that encodes such a bioactive agent or a protein that regulates production of a bioactive agent to regulate expression of the gene product. Heat sensitive gene promoters suitable for use in the invention method include the *E. Coli* and *Drosophila* heat shock promoters, and the like. Heating (even to low temperatures) can be made to either turn on, or turn off, the recombinant gene when the temperature is elevated, depending upon the selection of the transcription regulatory region, e.g., the promoter and other regulatory elements, as is known in the art. The temperature elevation may be achieved, as indicated above, utilizing an external energy source to transcutaneously (i.e., non-invasively or potentially invasively) heat the stent material and proximal cells.

The recombinant promoter/gene combination DNA can be transfected into the cells of interest near the implant site, or alternatively, may be eluted from the stent or implant device to transfect, locally, proximal cells. Cells may also be externally transfected with the heat sensitive promoter and gene, and then implanted with the stent device, so that heating the device following implant will activate (or inhibit) the gene product directly. Heating can be done chronically over time, being available to the biologic site of interest as long as the recombinant cells survive at the implant site.

Optionally, the cells can be obtained from a donor or from the host subject to be treated, modified as above, and then reintroduced into the subject to be treated. In a presently preferred embodiment, the transplanted cells are "autologous" with respect to the subject, meaning that the donor and recipient of the cells are one and the same.

Genetically modified cells are cultivated under growth conditions (as opposed to protein expression conditions) until a desired density is achieved. Stably transfected mammalian cells may be prepared by transfecting cells with an expression vector having a selectable marker gene (such as, for example, the gene for thymidine kinase, dihydrofolate reductase, neomycin resistance, and the like), and growing the transfected cells under conditions selective for cells expressing the marker gene. To prepare transient transfectants, mammalian cells are transfected with a reporter gene (such as the *E. coli* β-galactosidase gene) to monitor transfection efficiency. Selectable marker genes are typically not included in the transient transfections because the transfectants are typically not grown under selective conditions, and are usually analyzed within a few days after transfection.

Genes that encode useful bioactive agents that are not normally transported outside the cell can be used in the invention if such genes are "functionally appended" to a signal sequence that can "transport" the encoded product across the cell membrane. A variety of such signal sequences are known and can be used by those skilled in the art without undue experimentation.

Gene transfer vectors (also referred to as "expression vectors") contemplated for use herein are recombinant nucleic acid molecules that are used to transport nucleic acid into host cells for expression and/or replication thereof. Expression vectors may be either circular or linear, and are capable of incorporating a variety of nucleic acid constructs therein. Expression vectors typically come in the form of a plasmid that, upon introduction into an appropriate host cell, results in expression of the inserted nucleic acid.

Suitable expression vectors for use herein are well known to those of skill in the art and include a recombinant DNA or RNA construct(s), such as plasmids, phage, recombinant virus or other vectors that, upon introduction into an appropriate host cell, result(s) in expression of the inserted DNA. Appropriate expression vectors are well known to those of skill in the art and include those that are replicable in eukaryotic cells and/or prokaryotic cells and those that remain episomal or those which integrate into the host cell genome. Expression vectors typically further contain other functionally important nucleic acid sequences encoding antibiotic resistance proteins, and the like.

The amount of exogenous nucleic acid introduced into a host organism, cell or cellular system can be varied by those of skill in the art. For example, when a viral vector is employed to achieve gene transfer, the amount of nucleic acid introduced can be increased by increasing the amount of plaque forming units (PFU) of the viral vector.

As used herein, the phrase "operatively associated with" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and promoter such that the transcription of such DNA is initiated from the promoter by an RNA polymerase that specifically recognizes, binds to, and transcribes the DNA.

Preferably, the transcription regulatory region may further comprise a binding site for ubiquitous transcription factor (s). Such binding sites are preferably positioned between the promoter and the regulatory element. Suitable ubiquitous transcription factors for use herein are well-known in the art and include, for example, Spl.

Exemplary eukaryotic expression vectors include eukaryotic constructs, such as the pSV-2 gpt system (Mulligan et al., (1979) *Nature*, 277:108–114); pBlueSkript® (Stratagene, La Jolla, Calif.), the expression cloning vector described by Genetics Institute (*Science*, (1985) 228:810–815), and the like. Each of these plasmid vectors is capable of promoting expression of the gene product of interest.

Suitable means for introducing (transducing) expression vectors containing heterologous nucleic acid constructs into host cells to produce transduced recombinant cells (i.e., cells containing recombinant heterologous nucleic acid) are well-known in the art (see, for review, Friedmann, *Science*, 244:1275–1281, 1989; Mulligan, *Science*, 260:926–932. 1993, each of which are incorporated herein by reference in their entirety). Exemplary methods of transduction include, e.g., infection employing viral vectors (see, e.g., U.S. Pat. Nos. 4,405,712 and 4,650,764), calcium phosphate transfection (U.S. Pat. Nos. 4,399,216 and 4,634,665), dextran sulfate transfection, electroporation, lipofection (see, e.g., U.S. Pat. Nos. 4,394,448 and 4,619,794), cytofection, particle bead bombardment, and the like. The transduced nucleic acid can optionally include sequences which allow for its extrachromosomal (i.e., episomal) maintenance, or the transduced nucleic acid can be donor nucleic acid that integrates into the genome of the host.

Bioactive agents suitable for delivery according to the invention methods include those which the mammalian body utilizes to stimulate angiogenesis, including those which regulate capillary formation in wounds and attract smooth muscle to coat and support the capillaries. Examples of such bioactive agents include vascular endothelial growth factor (VEGF), fibroblast growth factors (FGFs), particularly FGF-1, angiopoietin 1, thrombin, and the like. Additional examples of bioactive agents suitable for delivery according to the invention methods include anti-proliferative, anti-restenotic or apoptotic agents, such as platelet-derived growth factor-A (PDGF-A), transforming growth factor beta (TGF-β), nuclear factor-κβ (NF-κβ), an inducible redox-controlled transcription factor, and the like.

In another embodiment according to the present invention, there are provided temperature-sensing stents for measuring the flow of a liquid, such as blood, through the stent. The invention temperature sensitive stent is based upon the principle that a liquid (e.g., blood) flowing through stent is a cooling medium and that the amount of cooling of a stent that has been heated above body temperature is directly proportional to the flow rate of the liquid flowing through the stent. When the stent is implanted in a blood vessel, the invention temperature-sensitive stent can be used to measure and monitor the flow of blood in the blood vessel in a non-invasive manner.

The invention temperature-sensitive stent comprises a tubular stent body having attached thereto a heating mechanism that includes one to about six temperature sensors, with the temperature sensors attached at discrete spaced locations along the length thereof, each adapted for sensing the temperature at the discrete location, and a telemetering device for transcutaneously conveying the temperature sensed by each sensor to a monitor. Optionally, the monitor can transform the message from the telemetering device to a visible display, or record the message in some other readable format. The monitor generally is in communication with the energy source so that temperature information from the sensors is used to turn the energy source on and off to modulate and/or control the temperature of the invention stent.

Generally the stent comprises from two to about six with the temperature sensors spaced out along the length of the stent body. For example, the stent may comprise three heat sensors equally spaced along the length of the stent body. It is preferred that the temperature sensors have sufficient sensitivity to detect a temperature difference as small as 0.1° C. from one end of the stent to the other end. When the temperature sensor is a thermocouple or thermopile, temperature differences as small as 0.1° C. can be detected.

The invention temperature-sensing stent may further comprise surface features in the stent body adapted to promote an organized growth pattern of infiltrating cells as described herein.

In another embodiment, methods are provided for using the invention temperature-sensing stent to measure flow of a fluid through a body lumen into which the stent is implanted, for example blood flow through a blood vessel. The invention method for measuring flow of a fluid comprises implanting an invention stent temperature-sensitive stent, as described herein, into a body lumen having a flow of fluid therethrough, energizing the implanted stent transcutaneously to raise the temperature thereof above body temperature, monitoring transcutaneously the output from one or more of the temperature sensors upon cessation of the energizing to determine the cooling rate at the sensors, and obtaining the flow rate of the fluid from the cooling rate at the one or more sensors. To be useful in measuring the flow rate of fluid through the implanted stent, the stent body is generally sufficiently to raise the temperature of the stent about 2 to 12 degrees Centigrade above body temperature.

Determination of the fluid flow rate from the temperature information (e.g., the cooling rate of the fluid flowing through the stent) provided by the temperature sensors via the telemetry in the stent involves application of one or more mathematical algorithms, such as are well known in the art. Such algorithms generally take into account such parameters as the heat capacity properties of the fluid, the interior cross-sectional area of the stent body, the length of the stent, the distance between the relevant temperature sensors, the difference between temperatures sensed at any two locations along the length of the stent, the difference between the temperature sensed at any discrete location and body temperature, the neointimal thickness/area, and the like. When the fluid whose flow rate is to be determined is blood, the heat capacity of the blood may vary by patient when such factors as hematocrit, and the like, are taken into account. Equation I below can be used to obtain a fluid flow rate based on such parameters as follows:

$$dT/dx = (\rho_o P)A/Q \quad (I)$$

wherein T=temperature; x=distance of fluid flow; $\rho_o$=specific heat of fluid; P=power in to heat the stent; Q=flow rate; and A=cross-sectional area of the stent.

The invention will now be described in greater detail by reference to the following non-limiting examples.

EXAMPLE 1

Temperature vs. Variable Flow Rates

The concept of flow measurement by the temperature sensitive stent is based upon the principle that a liquid (e.g. blood) flowing through a stent is a cooling medium and that the amount of cooling of a stent that has been heated above body temperature is directly proportional to the flow rate of the liquid through the stent. This is expressed by Equation I above. To validate the use of the heated stent as a measure of flow rate, experimental data was obtained through the bench testing as follows.

Figure 5:
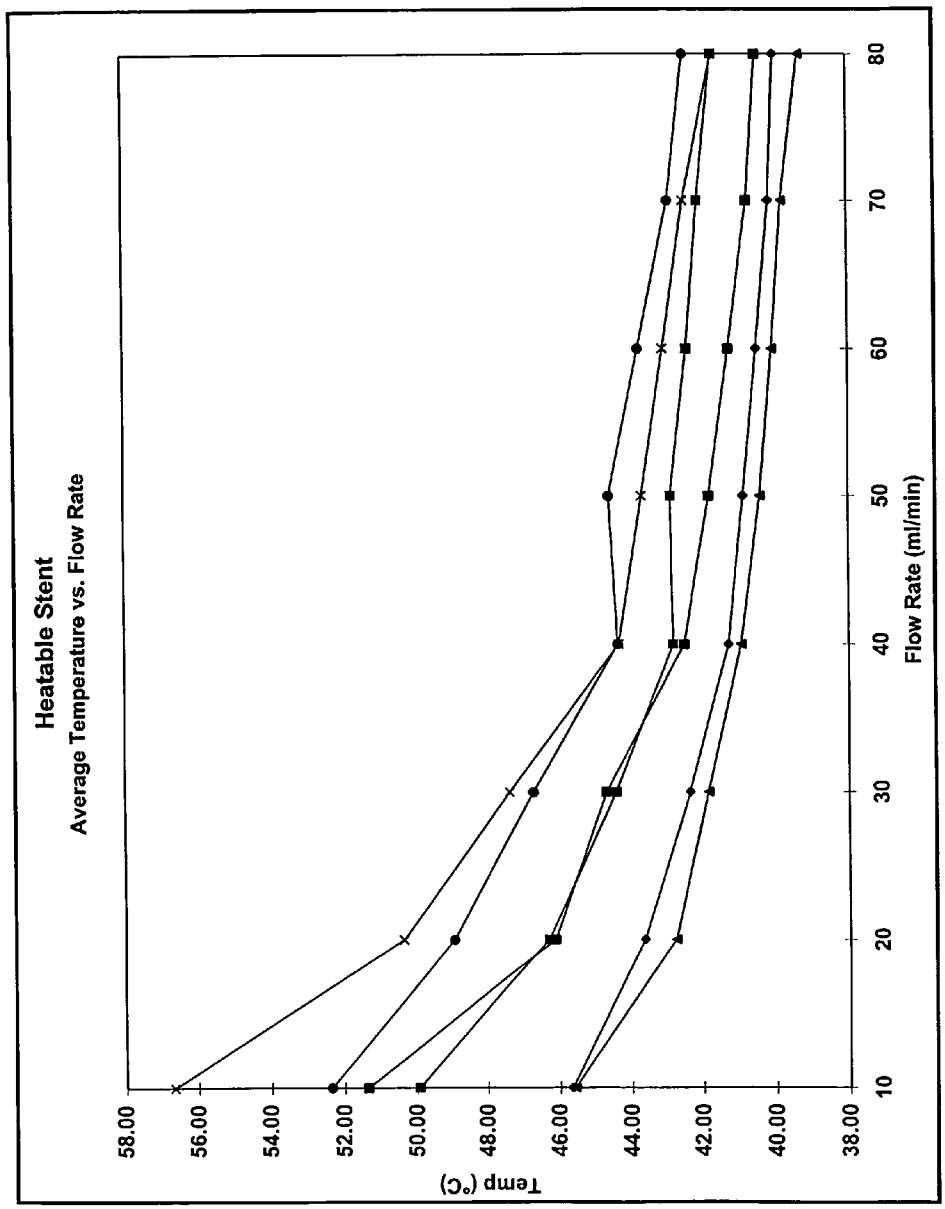
FIG. 5 is a graph showing the results of experiments conducted using the invention heatable stent to measure the rate of flow of blood through the stent. The temperatures shown (° C.) are the average for four data points for three equidistant temperature sensors on the stent, with "distal stent" representing the sensor distal to the heating element and "proximal stent" representing the sensor proximal to the heating element. Flow rate was measured with flow from the distal to the proximal sensor (Flow Distal) and from the proximal to the distal sensor (Flow Proximal). —x-=distal stent—flow distal; •=mid stent—flow distal; ■=mid stent—flow distal; ■=mid stent—flow proximal; ♦=distal stent—flow proximal; ▲=proximal stent—flow distal.

A GR2 type configuration stent was created using 38 AWG Nichrome resistance wire. 30 AWG Type J thermocouples were attached to the stent in three locations described as distal (furthest away from stent heating leads), mid and proximal. The stent was deployed in a simulated blood vessel made of silicone and submerged in a 37° C. distilled water bath. The water bath temperature was held constant during the testing. While a constant voltage of 11 V was applied to the stent leads, 37° C. distilled water was pumped via a peristaltic pump through the deployed stent/vessel assembly at flow rates of 10, 20, 30, 40, 50, 60, 70, 80 ml/min while temperature data was collected from each of the three thermocouples. The direction of the flow was then reversed and data was again collected for these flow rates. Temperature measurements were recorded for a total of three minutes. Four data points for each stent location were collected per minute. The data shown in Tables 1 and 2 below is the average of these four data points. The first three data points at each location were thrown out (time for stent temp to ramp to 11 V≈40 sec). FIG. 5 is a graph showing the average temperature plotted against flow rate (ml/min) for each of the three thermocouples.

TABLE 1

Flow Proximal to Distal

| Flow Rate (ml/min) | Distal Stent - Flow Distal Average Temp (° C.) | Mid Stent - Flow Distal Average Temp (° C.) | Proximal Stent - Flow Distal Average Temp (° C.) |
| --- | --- | --- | --- |
| 10 | 56.66 | 51.36 | 45.59 |
| 20 | 50.35 | 46.12 | 42.76 |
| 30 | 47.36 | 44.68 | 41.84 |
| 40 | 44.33 | 42.50 | 40.92 |
| 50 | 43.67 | 41.80 | 40.40 |
| 60 | 43.06 | 41.25 | 40.07 |
| 70 | 42.47 | 40.73 | 39.79 |
| 80 | 41.64 | 40.47 | 39.31 |

TABLE 2

Flow Distal to Proximal

| Flow Rate (ml/min) | Distal Stent - Flow Proximal Average Temp (° C.) | Mid Stent - Flow Proximal Average Temp (° C.) | Proximal Stent - Flow Proximal Average Temp (° C.) |
| --- | --- | --- | --- |
| 10 | 45.66 | 49.94 | 52.36 |
| 20 | 43.63 | 46.29 | 48.93 |
| 30 | 42.34 | 44.42 | 46.71 |
| 40 | 41.27 | 42.80 | 44.35 |
| 50 | 40.86 | 42.87 | 44.59 |
| 60 | 40.49 | 42.41 | 43.76 |
| 70 | 40.14 | 42.08 | 42.91 |
| 80 | 39.99 | 41.67 | 42.45 |

The values obtained from theoretical calculations using Equation I above correlated well with values obtained by these empirical tests.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment, operating procedures and end use, can be accomplished without departing from the scope of the invention itself as defined by the appended claims.

What is claimed is:

1. An implantable stent comprising a tubular stent body having a plurality of interconnected microholes distributed throughout said stent body substantially uniformly along the entire length of said stent body, said plurality of microholes being sufficiently small so as to promote an organized growth pattern of infiltrating cells throughout said stent body, and said stent body being otherwise substantially free of holes larger than said microholes, and said stent body is formed from a fibrous three dimensional non-woven matrix.

2. The stent according to claim 1 wherein the organized growth pattern is angiogenesis.

3. The stent according to claim 1 wherein the surface features comprise a plurality of depressions in the surface of at least a portion of the stent body.

4. The stent according to claim 3 wherein the depressions have an average volume per depression in the range from about 10 μm to about 100 μm.

5. The stent according to claim 3 wherein the depressions are in a regular pattern on at least the interior surface of the stent body.

6. The stent according to claim 5 wherein the pattern is selected to create turbulence in the flow of fluid through the stent body.

7. The stent according to claim 6 wherein the turbulence increases fluid shear stress upon the infiltrating cells.

8. The stent according to claim 1 wherein the surface features comprise a plurality of longitudinal pleats, grooves or channels in the stent body.

9. The stent according to claim 8 wherein the pleats, grooves, or channels have an average height or depth in the range from about 10 μm to about 100 μm and an average distance from center to center in the range from about 10 μm to about 100 μm.

10. The stent according to claim 8 wherein the pleats, grooves, or channels are spaced and sized to promote create fluid shear stress in flow of blood through the stent and/or to cause alignment of cells that infiltrate the pleats, grooves, or channels.

11. The stent according to claim 1 wherein the surface features comprise pores in the stent body having an average diameter in the range from about 30 microns to about 65 microns.

12. The stent according to claim 11 wherein the stent body is formed from a polymer or a non-woven matrix of metal fibers.

13. The stent according to claim 12 wherein the metal fibers are stainless steel, tantalum, elgiloy, nitinol, or a suitable combination thereof, and have a diameter in the range from about 1 micron to 25 microns.

14. The stent according to claim 12 wherein the non-woven matrix has a porosity of about 50% to about 85%.

15. The stent according to claim 14 wherein the porosity is at least about 70%.

16. The stent according to claim 1 wherein the surface features comprise an array of upstanding projections that promote shear turbulence in blood flow along at least a portion of the surface of the stent body.

17. The stent according to claim 16 wherein the projections have an average height of from about 10 μm to about 100 μm.

18. The stent according to claim 17 wherein the projections are an orderly array of hooks or stalks having a diameter to height ratio of from about 10:1 to about 100:1.

19. The stent according to claim 18 wherein the hooks or stalks have a uniform spacing of from about 10 μm to about 200 μm from center to center.

20. The stent according to claim 1 wherein the stent body is formed of a polymeric material having pores with an average pore diameter in the range from about 30 microns to about 65 microns.

21. The stent according to claim 1 wherein the surface features comprise a layer of a biocompatible substance that expands or thickens in an aqueous environment to assume a three-dimensional form, wherein the layer covers at least a portion of the surface of the stent body.

22. The stent according to claim 21 wherein the three dimensional form comprises an array of upstanding projections.

23. The stent according to claim 21 wherein the layer comprises a hydrogel.

24. The stent according to claim 21 wherein the three dimensional form is porous.

25. The stent according to claim 21 wherein the expandable substance is a hydrogel.

26. The stent according to claim 1 wherein the surface features comprise a pattern of hydrogel markings on at least a portion of the surface of the stent body.

27. The stent according to claim 26 wherein the pattern of markings comprises a plurality of dots, lines, curvilinear tracings, or a mixture thereof.

28. The stent according to claim 27 wherein the markings are distributed over the interior surface of the stent body.

29. The stent according to claim 1 wherein the stent is diametrically adjustable.

30. The stent according to claim 1 wherein the stent further comprises a transcutaneously energized heating mechanism attached to the stent body.

31. The stent according to claim 30 wherein the heating mechanism is adapted to controllably heat the stent to temperatures from about 38° C. to about 49° C. when the stent is implanted.

32. The stent according to claim 31 wherein the heating mechanism comprises a thermostat/heat regulator.

33. The stent according to claim 32 wherein the thermostat/heat regulator comprises one or more heat sensors and telemetering device for conveying the temperature sensed by each sensor.

34. The stent according to claim 33 wherein the telemetering device comprises an antenna coil wrapped about the surface of the stent and a hybrid integrated circuit chip in communication with the antenna coil, whereby energy picked up by the antenna coil powers the hybrid circuit.

35. The stent according to claim 33 wherein the thermostat/heat regulator comprises at least two heat sensors located at opposite ends of the stent body.

36. The stent system according to claim 34 wherein each of the sensors produces a temperature output signal corresponding to the temperature sensed and wherein the stent system further comprises a monitor in spaced juxtaposition to the stent for transcutaneously receiving the output signal from each sensor.

37. The stent according to claim 34 wherein the heat sensors have sufficient sensitivity to detect a temperature difference as small as 0.1° C. from one end of the stent to the other end.

38. The stent system according to claim 37 wherein the energy source delivers electromagnetic energy to the stent in the form of radio frequency energy, microwave energy, or a magnetic field.

39. A stent system comprising a stent according to claim 37 in spaced juxtaposition to an energy source for transcutaneously applying energy to the stent, thereby causing the temperature of the stent to increase to the temperature from about 38° C. to about 49° C.

40. The stent system according to claim 38 wherein the monitor is in communication with the energy source and signals from the monitor activate the energy source.

41. A stent system comprising a stent according to claim 1 in spaced juxtaposition to an energy source for transcutaneously applying energy to the stent, thereby causing the temperature of the stent to increase to a temperature above body temperature.

42. An active stent comprising a stent according to claim 1 and further comprising live cells growing in said interconnected microholes.

43. The active stent according to claim 42 wherein the live cells are selected from the group consisting of endothelial cells, smooth muscle cells, leukocytes, monocytes, epithelial cells, polymorphonuclear leukocytes, lymphocytes, basophils, fibroblasts, stem cells, epithelial cells and eosinophils.

44. The active stent according to claim 43 wherein the live cells are smooth muscle cells, epithelial cells, or endothelial cells.

45. The active stent according to claim 42 wherein the stent further comprises a transcutaneously energized heating mechanism adapted to control the heating of the stent to a temperature sufficient to cause the live cells to increase production of one or more bioactive agents.

46. The active stent according to claim 45 wherein the bioactive agent stimulates angiogenesis and/or capillary formation.

47. The active stent according to claim 46 wherein the bioactive agent is vascular endothelial growth factor (VEGF), a fibroblast growth factor (FGF), angiopoietin 1, or thrombin.

48. The active stent according to claim 45 wherein the bioactive agent modifies vascular structure in the hematologic system.

49. The active stent according to claim 48 wherein the bioactive agent modifies platelet function.

50. The active stent according to claim 45 wherein the bioactive agent is an anti-proliferative, anti-restenotic, or apoptotic agent.

51. The active stent according to claim 50 wherein the bioactive agent is nitric oxide.

52. The active stent according to claim 45 wherein the agent increases production of nitric oxide in the cells in or around the stent.

53. The active stent according to claim 42 further comprising means carried by the stent body for telemetering stent temperature information to an external energy source.

54. The stent according to claim 1, wherein said stent body is penetrated with said microholes.

55. The stent according to claim 1, wherein said microholes extend throughout said stent body so as to promote cell growth outward into said stent tube and into attachment with cells at either end of said stent.

56. A method for measuring flow of a fluid through a body lumen, said method comprising:
 implanting a stent according to claim 33 into a body lumen having a flow of fluid therethrough,
 energizing the implanted stent transcutaneously to raise the temperature thereof above body temperature,
 monitoring transcutaneously the output from one or more of the temperature sensors upon cessation of the energizing to determining the cooling rate at each of the one or more sensors, and
 obtaining the flow rate of the fluid through the stent from the cooling rate at the one or more sensors.

57. The method according to claim 56 wherein the temperature of the stent is raised from 0.1° C. about 12° C. above body temperature.

58. The method according to claim 56 wherein the fluid is blood and the stent is implanted in a blood vessel.

59. The method according to claim 56 wherein the cooling rate is determined at least two of the sensors and the flow rate is obtained as a function of the distance between the two sensors.

60. The method according to claim 56 wherein the cooling rate is determined using the temperature difference between at least two of the temperature sensors.

61. The method according to claim 56 wherein the method is repeated periodically to monitor occlusion of the lumen.

62. A method for treating a tubular body organ in a subject in need thereof said method comprising:
 promoting the ingrowth of living cells in a stent having a plurality of interconnected microholes distributed within said stent body substantially uniformly along the entire length of said stent body, said plurality of microholes being sufficiently small in size so as to promote ingrowth of the cells, and said stent body being otherwise substantially free of holes larger than said microholes, and,
 implanting the stent into the tubular organ of the subject prior to or following the promoting of the ingrowth of the living cells so as to treat the tubular organ, and said stent body is formed from a fibrous three dimensional non-woven matrix.

63. The method according to claim 62 wherein the living cells are donor or autologous cells.

64. The method according to claim 63 wherein the living cells are autologous.

65. The method according to claim 62 wherein the treatment further comprises promoting or inhibiting angiogenesis within the stent body.

66. The method according to claim 62 wherein the body organ is a blood vessel.

67. The method according to claim 62 wherein the treating comprises holding the cells in a specific pattern or stimulating the growth of the cells into an organized growth pattern.

68. The method according to claim 67 wherein the organized growth pattern develops into an organized cellular structure within the stent body.

69. The method according to claim 62 wherein the stent can be heated by transcutaneously applied energy and the method further comprises transcutaneously energizing the heating of the stent to a temperature above normal body temperature sufficient to cause the living cells to express one or more bioactive agents.

70. The method according to claim 69 wherein the one or more bioactive agents promotes or inhibits angiogenesis within the living cells growing in the stent.

71. The method according to claim 69 wherein at least some of the living cells contain a DNA construct encoding and expressing a bioactive agent under the control of an operatively associated exogenous heat shock promoter.

72. The method according to claim 71 further comprising turning the promoter on or off by controlling the heating of the stent.

73. The method according to claim 71 wherein the heat shock promoter is derived from *E. Coli* or *Drosophilia*.

74. The method according to claim 71 wherein the treating further comprises chronically releasing the bioactive agent on demand by transcutaneously energizing the stent.

75. The method according to claim 69 wherein the temperature to which the stent body is heated remains below a value lethal to the living cells.

76. The method according to claim 75 wherein the temperature to which the stent body is heated is in a range from about 38° C. to about 49° C.

77. The method according to claim 62 wherein the living cells are endothelial cells, smooth muscle cells, leukocytes, monocytes, polymorphonuclear leukocytes, lymphocytes, basophils, fibroblasts, stem cells, epithelial cells or eosinophils.

78. The method according to claim 62, wherein said stent body is penetrated with said microholes.

79. The method according to claim 62, wherein after the implanting of said stent, said ingrowth of living cells is promoted such that said cells grow outward into said stent tube and into attachment with cells at either end of said stent.

* * * * *